(12) United States Patent
Fernandez

(10) Patent No.: US 8,656,565 B2
(45) Date of Patent: Feb. 25, 2014

(54) FASTENING SYSTEM

(76) Inventor: Michael Fernandez, Falls Church, VA (US)

( * ) Notice: Subject to any disclaimer, the term of this patent is extended or adjusted under 35 U.S.C. 154(b) by 343 days.

(21) Appl. No.: 12/905,483

(22) Filed: Oct. 15, 2010

(65) Prior Publication Data

US 2011/0088225 A1 Apr. 21, 2011

Related U.S. Application Data

(60) Provisional application No. 61/252,465, filed on Oct. 16, 2009.

(51) Int. Cl.
*A44B 18/00* (2006.01)

(52) U.S. Cl.
USPC ............................................ 24/442; 428/100

(58) Field of Classification Search
None
See application file for complete search history.

(56) References Cited

U.S. PATENT DOCUMENTS

| | | | |
|---|---|---|---|
| 5,362,303 A | | 11/1994 | Jasen et al. |
| 5,586,595 A | * | 12/1996 | Takizawa et al. ............. 160/330 |
| 6,279,168 B1 | | 8/2001 | Bean |
| 6,491,431 B2 | | 12/2002 | Merton |
| 6,568,981 B1 | | 5/2003 | Chang |

* cited by examiner

*Primary Examiner* — Jack W. Lavinder
(74) *Attorney, Agent, or Firm* — Andrew C. Aitken

(57) ABSTRACT

The present invention is directed to a method for maintaining a fastening system and a fastening kit for providing variable fastening ability and structural longevity. The interrelationships between surfaces bearing strong closure deformations and weak closure deformations permit displacement of multiple member systems with reliable displacement generally between a single pair of members.

10 Claims, 4 Drawing Sheets

FASTENING SYSTEM

RELATED APPLICATIONS

The present application claims priority from U.S. Provisional Patent Application Ser. No. 61/252,465 titled Fastening System, filed Oct. 16, 2009, which is incorporated herein by reference.

FIELD OF THE INVENTION

The present invention relates to the field of fastening systems and more specifically to the field of hook-and-loop joining devices.

BACKGROUND

George de Mestral while walking his dog in the woods noticed that burrs tenaciously gripped his dog's fur. He replicated the junction of the burrs and the fur on two strips of fabric with one strip containing engaging members (the "hook" strip) and the other strip containing fabric loops (the "loop" side). He created the portmanteau VELCRO out of "velour" meaning looped fabric and "crochet" meaning hook.

Early versions of the hook-and-loop fasteners were woven and exhibited a "scratchy" hook side that consisted of many randomly oriented, nylon-coated woven hooks cut eccentrically to allow the hooks to engage the many loops on the loop side. The hook side was scratchy and annoying to the touch, clung to unintended materials, and possessed a Standard Velcro Peel Strength (SVPS).

Decades passed and a wide variety of engineered hooks (molded or extruded in an essentially planar plastic) arose to supplement the existence of the standard hook-and-loop fastener. Most of these new hook shapes resembled the crests of waves, others resembled mushroom caps, and yet others possessed novel shapes (e.g. bulbous parallelograms on a stick, anchors, etc.). The varying shapes were invented for the hook side to vary the peel strength, shear strength, cycle life, and perceived roughness to the touch, as well as reduce the likelihood of catching on unintended looped surfaces, like expensive sweaters, pantyhose, etc.

Woven hook was commonly adhered to a flexible surface by sewing the material backing of the hook strip to some other substrate (material, cloth, leather, vinyl, etc). Woven hook embodiments included many flaws: woven hook was difficult to sew and caused snags in the sewing machine thread; often the hammer of the sewing machine would deform or crush some or many of the hooks; a manufacturer had to ensure that the peel strength of the hook-and-loop system did not exceed the tensile strength of the threads anchoring the hook strip to the substrate—otherwise upon strip removal the hook strip would pull itself from threads holding it to the substrate. Comparatively speaking, the loop strip of hook-and-loop fasteners acts similar to any other rigid material; it is simple to sew, and it does not snag thread. Where perimeter sewing is insufficient to exceed the peel strength of the hook-and-loop system, the system can be anchored with grids, zig-zags, reinforcement points for large surface areas, etc. Although increasing the thread quantity substantially increases the ability of the hook-and-loop system to adhere to a backing material, excess threading may diminish the adherence between the hooks and loops.

For impenetrable and prohibitively penetrable backings such as dashboards, walls, tables, and other non-sewable objects, woven hook was backed with an adhesive that varied in tenacity depending on the manufacturer and product line. More often than not, repeated disengagement cycles would eventually cause the hook strip to peel from the substrate. Most adhesives need some sort of pressure or impact force to activate the molecules of the adhesive to adhere the molecules of the backing. For example, most shoe soles bonded to a shoe with contact cement are banged with a hammer to activate the bonds of the cement. In adhesive bonded hook-and-loop applications, one might apply force to the loop side with impunity; the hook side, however, includes more delicate structures more easily crushed, damaged, or broken. This principle applies to compressive forces exerted via pinch rollers, and many other common fabrication devices.

Considerable deliberation precedes use of hook-and-loop fasteners in design applications: the hook side is widely despised by consumers. No one wants to touch it and it ought not dangle free due to its tendency to catch and snag something of value. For example, in notebooks and briefcases the hook side was usually reserved for the flap. In the minority of times when this design was not adopted, it usually followed that the flap was intended to dangle freely. Either way, entire board rooms of designers, marketers, and product specialists would occasionally spend countless hours deciding which side would house the dreaded hook side (e.g., tablet PC handheld cases, Palm Pilot cases, cell phone cases, clothing flaps, etc.).

For variable circumference applications such as shoe closures or neck closures for motorcycle jackets, some portion of unused hook surface will always remain exposed (i.e. unmated) on the flap side for small necks or narrow feet; or if the hook surface is placed on the non-flap side, it is often exposed for large necks and high arches, thereby catching and fraying things like scarves or woven trousers. It is often the case that no clear choice exists for placement of the hook surface and the placement of the loop surface.

Many outdoor garments use hook-and-loop closures. Laundering them is cumbersome as consumers fear mingled other garments with garments bearing hook-and-loop closures; its neighbors are in constant peril of getting snagged by the hook side. If one attempts to solve the garment mutilation problem by engaging the hook side onto its intended loop side—as in, say, a coat sleeve—then the dirty crevice formed by the fold does not get clean. Some garments, like sweaters with hook-and-loop closures, are prime candidates for mutilation should a fastened hook strip inadvertently disengage from its loop and catch the fabric of the sweater during the washing machine's agitation cycle.

Many times, the hook-and-loop closures lose their useful peel strength more rapidly than the item to which they are attached lose their utility, especially in tough garments, leather briefcases, etc. Frequently a new hook-and-loop system cannot be reattached cost effectively, rendering the entire item useless. Spent hook-and-loop systems may be characterized by a loop side frayed to present a "fuzzy" surface or severed hooks that break or become disoriented to lose their strength.

Therefore, there is a need for a fastening system that allows prolonged use of an item accommodating the fastening system, creates diversity in the closure strength of the fastening system, increases the desirability of hook-and-loop fasteners, decreases the likelihood of unintended fastening to foreign objects, minimizes assembly complexity, minimizes article cost, and that is replaceable.

SUMMARY

The present invention is directed to a method for maintaining a fastening system and a fastening kit for providing variable fastening ability and structural longevity. The kit includes a supportive backing, base closure member, an adapter, and a target member.

The supportive backing is a material upon which the base closure member is fastened. The fastening occurs via a permanent, or near-permanent, base binding system. The base closure members include a base closure surface with base closure deformations. Deformations of the present invention include structural members that are adapted to interlock with mating structural members to retain two objects. Preferred deformations of the present invention include VELCRO hook projections and loop receipt structures and mushroom/aperture fastening systems.

The adapter is a substantially planer closure member with a strong adapter closure surface having deformations and a weak adapter closure surface with deformations. The target member includes a weak target closure surface with deformations. The deformations of the weak adapter closure surface and the weak target closure surface are of a grade requiring a lower initial removal threshold than the deformations of the strong adapter closure surface and the base closure surface. Similarly the deformations of the strong adapter closure surface and the base closure surface are of grade requiring a lower initial removal threshold than the binding system maintaining the base closure member upon the supportive backing. It is preferred that each layer of fastened surfaces—i.e., target member and adapter; adapter and base member; and base member and supportive backing—is joined with deformations having a removal threshold that does not disturb the structural integrity of a more strongly bound adjacent layer.

The adapter may further include substantially planar dimensions that accommodate a strong target closure surface with deformations and that are positioned opposite the weak target closure surface. Such a target member is further used in conjunction with an object closure member with deformations on an object closure surface. The object closure member is bound to a buttress by an object binding system.

All weak closure surfaces of the present invention are adapted to releasably attach to a second weak closure surface; all strong closure surfaces of the present invention are adapted to releasably attach to a second strong closure surface. The deformations include weak-weak and strong-strong conceptually characterize an important aspect of the present invention: the variable attachment nature of closure surfaces. The strong closure surfaces cooperate with other strong closure surfaces to allow an initial removal threshold greater than the interaction between two weak closure surfaces, yet allow an initial removal threshold less than that of the binding systems. It is preferred that the initial removal threshold between weak closure surface is less than half of the initial removal threshold between strong closure surfaces, and the initial removal threshold between strong closure surfaces should be less than half of the initial removal threshold provided by the binding systems.

Therefore, it is an aspect of the present invention to provide a fastening system that allows prolonged use of an item accommodating the fastening system.

It is a further aspect of the present invention to provide a fastening system that creates diversity in the closure strength of the fastening system.

It is a further aspect of the present invention to provide a fastening system that increases the desirability of hook-and-loop fasteners.

It is a further aspect of the present invention to provide a fastening system that decreases the likelihood of unintended fastening to foreign objects.

It is a further aspect of the present invention to provide a fastening system that minimizes assembly complexity.

It is a further aspect of the present invention to provide a fastening system that minimizes article cost.

It is a further aspect of the present invention to provide a fastening system that is replaceable.

It is a further aspect of the present invention to provide a variable fastening system.

These aspects of the invention are not meant to be exclusive. Furthermore, some features may apply to certain versions of the invention, but not others. Other features, aspects, and advantages of the present invention will be readily apparent to those of ordinary skill in the art when read in conjunction with the following description, and accompanying drawings.

DETAILED DESCRIPTION

Figure 1:
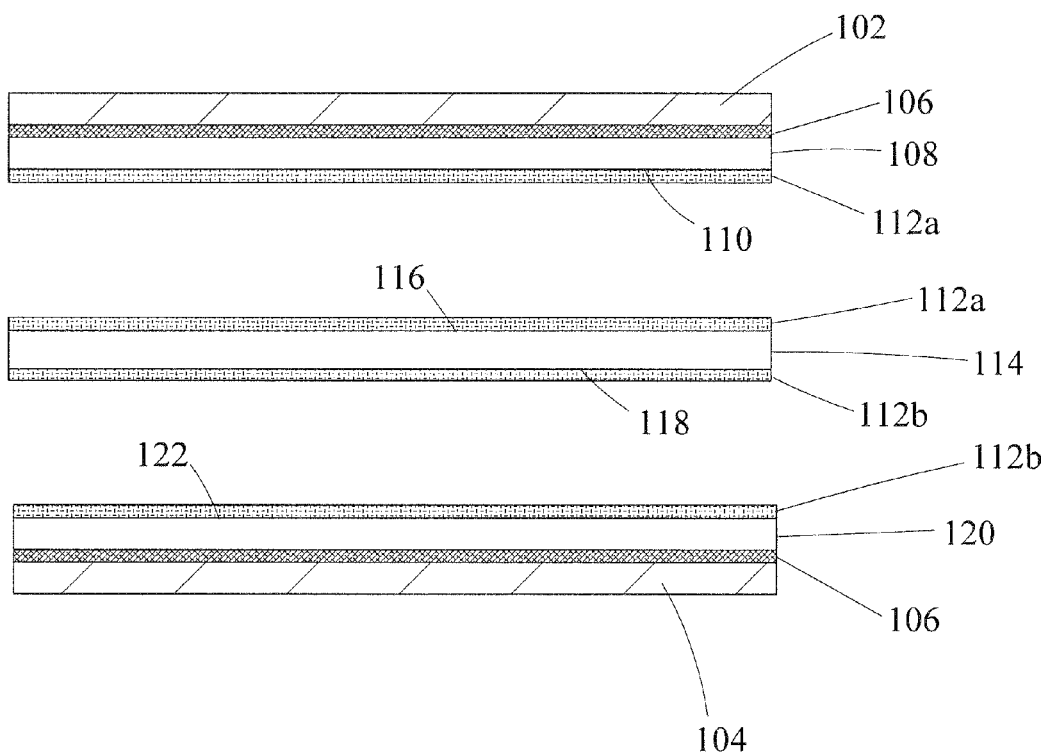
FIG. 1 is a side, plan representation of the system of the present invention.
Figure 5:
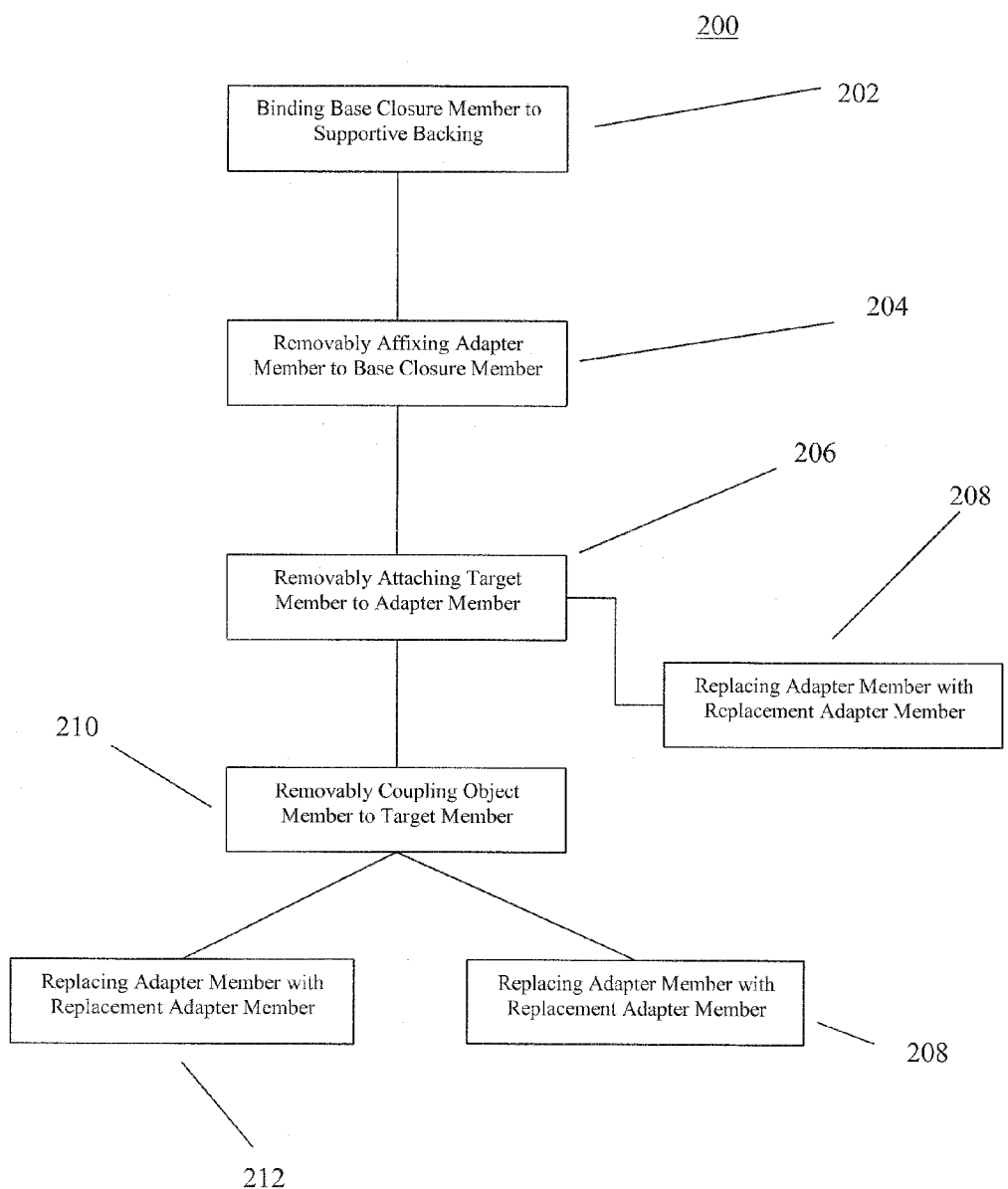
FIG. 5 is a view of the method of the present invention.

Referring first to FIG. 1 in conjunction with FIG. 5, an embodiment of the fastening system kit 100 and fastening method 200 are shown. In reference to the fastening system, it is meant the components of the multiple embodiments of the kit 100 inclusive of methods 200 of release and attachment of those components. The kit 100 includes a supportive backing 102 that is bound to a base closure member 108, or base, by a binding system 106.

The supportive backing 102 is any surface capable of receiving the base 108. Preferred materials for a supportive backing 102 include any conventional materials used to manufacture clothing. Other supportive backings 102 may include materials commonly used to accept a temporarily affixed object, such as a white board, a wall, furniture, carrying cases, etc. The supportive backing retains 202 the base 108 with a binding system 106. Although the present invention includes many means of affixing one component to another, the differences in the attachment strengths, i.e. initial removal threshold, preferably vary. The binding system 106 is the strongest means for affixing two components together, and in its most preferred state, is permanent or near-permanent. Examples of preferred binders for use in the binding system 106 include thread, chemical adhesives, mechanical attachment structures, and other attachment members capable of sturdy, long-term permanent affixation. Permanent affixation for the purposes of the present disclosure includes any affixation commonly used in the art to establish a long-lasting bond that is not meant to be severed in everyday use of the article bearing it. The binding system 106 of the present invention will vary with the base 108 and supportive backing 102 used therewith.

The base closure member 108 of the present invention includes a base closure surface 110. The base closure surface 110 of the base 108 is oriented away from the supportive backing 102 and is preferably planar. Upon the base closure surface 110 strong closure deformations 112a are placed or formed. Closure deformations 112 of the present invention include structural members that are adapted to interlock with mating structural members to retain two objects. Preferred deformations of the present invention include VELCRO hook projections and loop receipt structures and mushroom/aperture fastening systems. Deformation refers to any aberration in a structure that allows structural cling to a second member dimensioned to accept it.

An adapter member 114, or adapter, of the present invention is a substantially planer member that adheres 204 to the base closure member 108. By substantially planar, it is meant that the body includes dimensions that are thin to a degree that the dimensions do not interfere with the ability of the system 100 to maintain a substantially-flush, closed configuration. Preferred widths of the adapter are less than 0.3 millimeters, but may range up to 13.0 mm in some applications. Other, more industrial, applications of the present invention may utilize adapters 114 of thickness greater than 13.0 mm. The adapter 114 includes two surfaces, which may have dimensions generally without restriction: a strong adapter closure surface 116 and a weak adapter closure surface 118. The terms strong and weak when used in the present disclosure are meant to be relative, one to the other, and unless otherwise stated do not infer specific ranges. Indeed, the terms "strong" and "weak" rather than necessarily referring to a single surface refer instead to the relative cling strength between two surfaces. That is to say, two surfaces that provide a relatively strong cling are necessarily composed of strong closure surfaces irrespective of the type of closure deformations on that surface. The strong adapter closure surface 116 includes strong deformations 112a adapted to mate with the strong deformations 112a of the base 108. The weak adapter closure surface 118 includes weak closure deformations 112b adapted to mate with a target member 120, or target.

The target member 120 of the present invention includes a weak target closure surface 122. The weak target closure surface 122 includes weak closure deformations 112 thereon adapted to mate with the deformations of the weak adapter closure surface 118. The target member 120 in embodiments of the present invention may be attached to a buttress member 104, or buttress. The buttress 104 is any surface capable of receiving either the target member 120 or some other member bearing closure deformations. Preferred materials for a buttress 104 include any materials that may be used as the supportive backing 102. The buttress 104 retains the target 120 via the binding system 106.

The mating weak closure deformations of the present invention have a lower initial removal threshold, often referenced in the art as "peel strength," than the mating strong closure deformations; and the mating strong closure deformations allow an initial removal threshold less than that of the binding systems. Peel strength may be measured and compared using any of the peel strength tests available in the art, including T-Peel, 90-degree Peel, and the like. When used for comparing a first peel strength of two surfaces of the present invention with a second peel strength between another two surfaces, it is preferred for purposes of clarity that the same peel strength basis is used. It is preferred that the initial removal threshold between weak closure surface is less than half of the initial removal threshold between adjacent strong closure surfaces, and it is further preferred that the initial removal threshold between strong closure surfaces should be less than half of the initial removal threshold provided by the binding systems.

Table 1 shows initial removal values between the components of the present invention. The mating weak closure deformations of, for example, the target member 120 and the adapter 114 join to have an initial removal value designated $\gamma$, where $\gamma_1$ represents an initial removal value between an original target member and an original adapter, and $\gamma_2$ represents an initial removal value between the target member and a replacement adapter. The mating strong closure deformations of, for example, the adapter 114 and the base closure member 108 join to have an initial removal value designated $\beta$, where $\beta_1$ represents an initial removal value between a base closure member and an original adapter, and $\beta_2$ represents an initial removal value between a base closure member and a replacement adapter. A removal value between the base closure member 108 and the supporting backing 102 is referenced as $\alpha_1$, and a removal value between the target surface and the buttress 104 may be referenced as $\alpha_2$ when applicable as adapted for near-permanent to permanent affixation of the target.

TABLE 1

(In Pounds per Inch-width)

| $\alpha_1$ | $\beta_1$ | $\gamma_1$ | $\alpha_2$ | $\beta_2$ | $\gamma_2$ |
|---|---|---|---|---|---|
| 10.0+ | 4.0 | 0.5 | 10.0+ | 4.0 | .25 |
| 15.0+ | 3.5 | 0.25 | 15.0+ | 3.5 | .5 |
| 12.0+ | 3.0 | 0.25 | 12.0+ | 3.0 | .25 |
| 20.0+ | 2.5 | 0.25 | 12.0+ | 2.5 | .1 |
| 6.0+ | 2.0 | 0.2 | 6.0+ | 2.0 | .2 |
| 6.0+ | 2.5 | 0.1 | 6.0+ | 2.5 | .1 |

Figure 2:
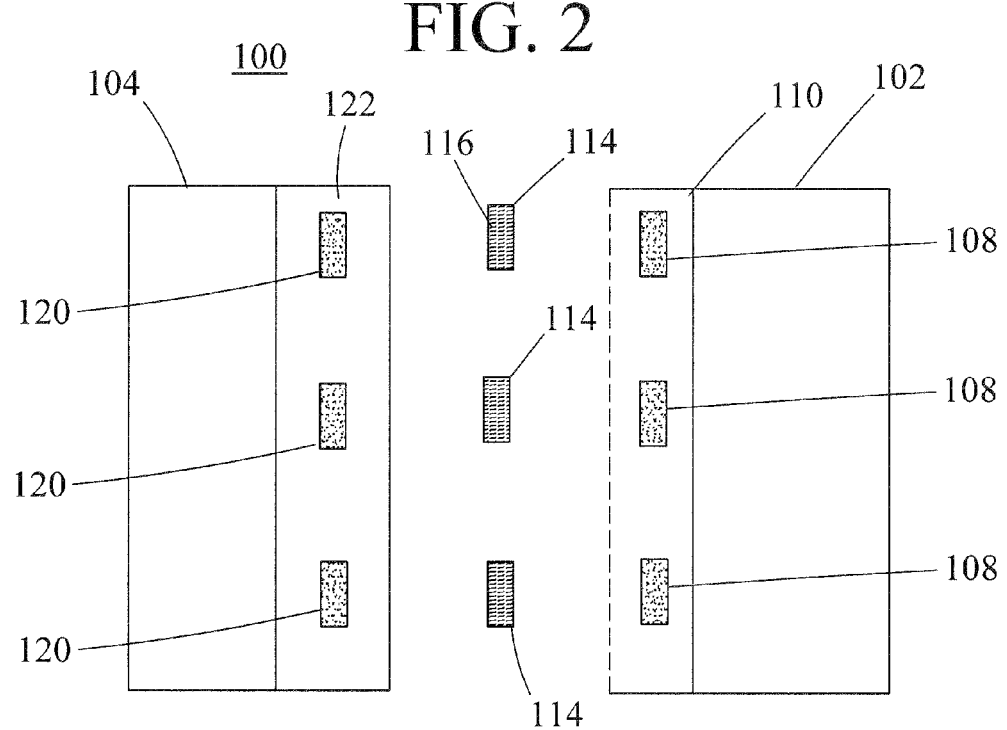
FIG. 2 is a top, plan representation of the system of the present invention.
Figure 3:
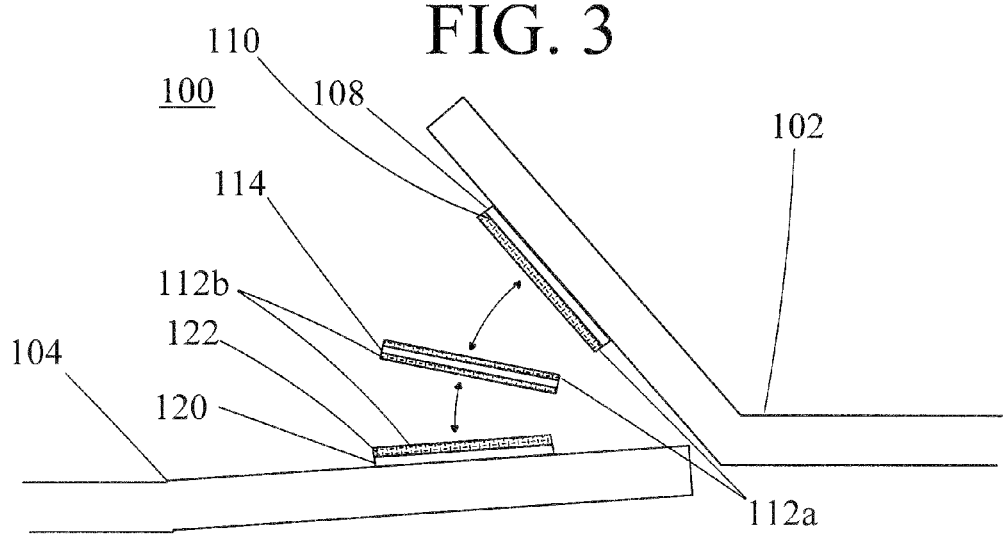
FIG. 3 is a side, plan representation of the system of the present invention.

Arranging the closure deformations in multiple layers of variable initial removal strengths allows multiple advantages. An example of the utility of the arrangement of the present invention depicted in FIG. 1 includes fastening systems for clothes. With reference to FIGS. 2 and 3, normally an article of clothing may include a two-component set of mating closure deformations that allow a user to fasten/remove two layers at her convenience. However, closure deformations often have lifetime use limits approaching four orders of magnitude, e.g. 8000 peels/life. As the closure deformations approach their use limits, the article becomes less usable due to the deterioration of the closure deformations. It is advantageous to include the negligibly-thick adapter 114 of the present invention in such circumstances to accord the article of clothing a longer span of usefulness and maintain the aesthetic qualities of the garment.

It is not enough, however, to merely include a strip of material bearing two closure deformation surfaces; instead, it is preferred that the adapter 114 include, and the base member 108 support, a high-grade closure deformation surface opposite of lower grade deformation surface. Such a differential surface pairing allows a user to fasten the high-grade deformations once per life-cycle, or a substantial portion thereof, of the adapter's lower grade closure deformations. As the strength of the high-grade closure deformations increases, so too does the likelihood that a user wishing to disjoin the fastening system correctly and consistently disjoins the fastening system between the weak closure deformations. However, as the initial removal strength of the strong closure deformations increases, so do does the likelihood that removing the adapter may cause structural damage to the (intended) permanent binding system that fastens the base to the supportive backing. Rather than wear out the deformations of the article of clothing, the deformations of the adapter wear out. In a shirt, by way of example, the supportive backing 102 and buttress 104 may be layers of the shirt. When the target member 120 is located on the buttress 104, it is preferred that the weak target closure members include only the loop portions of a hook and loop fastener, and the weak adapter closure members include only the hook portions of a hook and loop fastener. It is well established that hook closure deformations wear out more quickly than the loop closure deformations. Thus, a three-member fastening system may substantially prolong the use of the two, more permanent members.

Figure 4:
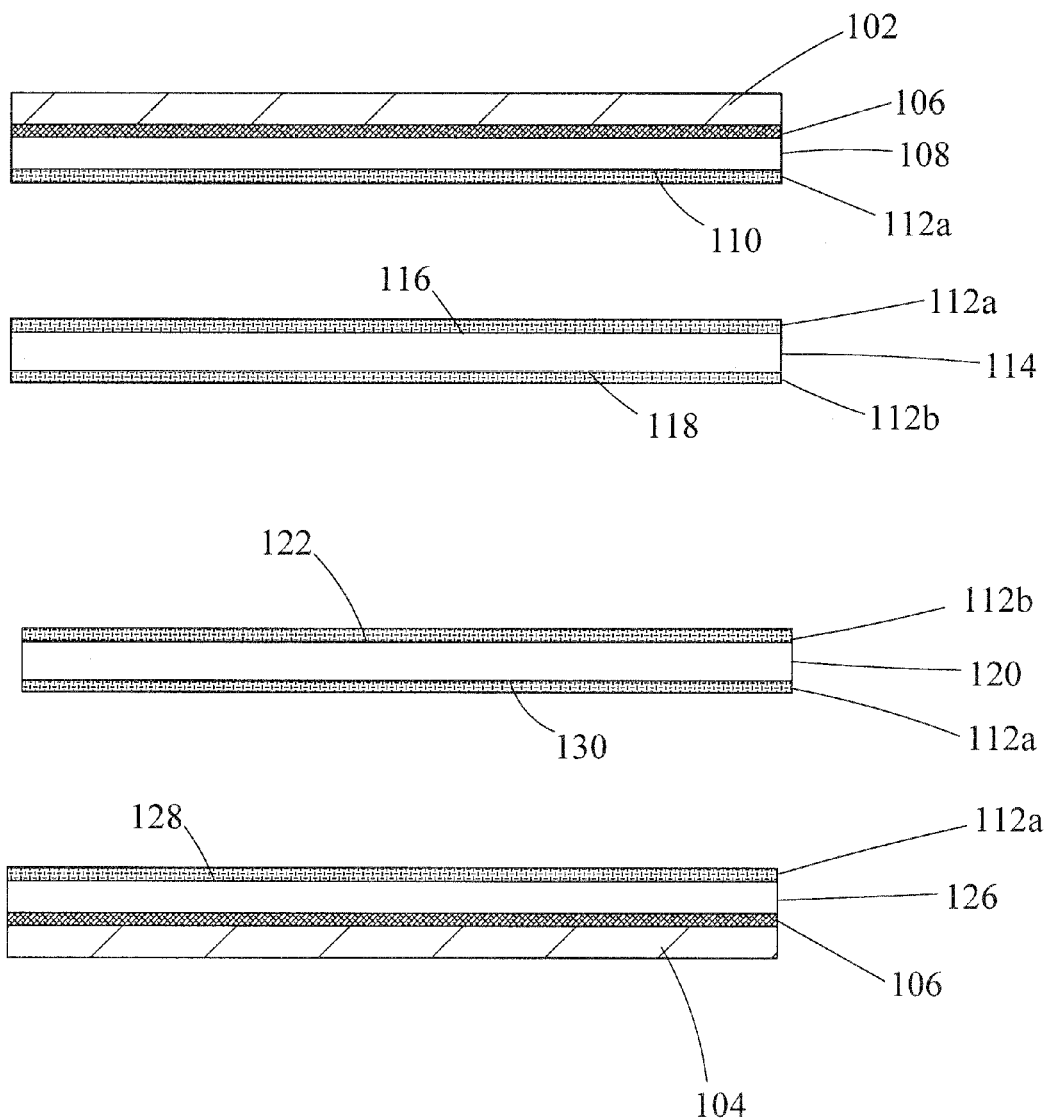
FIG. 4 is a side, plan representation of the system of the present invention.

In situations where a user seeks to more fully protect two permanent fastening members, the user may opt to include a four member system as is shown in FIG. 4 in conjunction with FIG. 5. In addition to the base member 108, adapter member 114, and target member 120, the four-member fastening system 100 includes an object member 126 and a freestanding target member 120. As with all embodiments, the target member 120 removably affixes 206 to the adapter member 114. The object member 126 acts to receive the target member 120 too. The object member 126 of the four-member system 100 includes an object closure surface 128 and having strong closure deformations 112*a* thereon.

The target member 120 of the four member system includes a substantially planer body with a strong target closure surface 130. The strong target closure surface 130 includes strong closure deformations 112*a* adapted to mate with the strong closure deformations 112*a* of the object closure surface 128. The strong target closure surface 130 of the target member 120 removably couples 210 to the object closure surface 128 of the object member 126. The four member fastening system includes variable layers of component fastening such that the object member 126 and the buttress 104 need only fasten once per life cycle of the more easily manipulated weak closure deformations. In addition to the natural deterioration of the initial removal strength caused by the inherent stresses involving in peeling clinging members one from the other, deterioration sought to be ameliorated by the present invention further includes particle accumulation caused by the clinging nature of the closure deformations. A prime example of such accumulation includes aggregation of cotton strands collected by fastening systems during a drying cycle.

Although this disclosure references target members 120 and adapter members 114, in many embodiments of the present invention the target member 120 may be the equivalent of the adapter member 114. The use of the terms "target" and "adapter" can distinguish the two members from each other structurally, or when one or both are present in wafer form, may instead merely be distinguished in terms of order applied to the system 100. Similarly, the terms "buttress" and "supportive backing" when used in conjunction with layers are utilized more for clarity of explanation rather than to identify distinct structural attributes or components. Target members and adapter members may be identical in one or all respects, and buttress layers and supportive backing layers may be identical in one or all respects.

Returning to FIG. 5, the present invention further includes a method that utilizes replacement members to substitute worn or undesirable members. The replacement members may include replacement adapter members, which include the characteristics of adapter members; or the replacement members may include replacement target members, which include the characteristics of target members in their distinct, wafer form. The replacement members may mimic the initial removal thresholds of the surfaces of members that they replace, or alternatively they may include initial removal thresholds that alter the characteristics of the system. A replacement adapter member allows a user to replace 208 a worn adapter member with a new adapter member. A replacement target member allows a user to replace 212 a worn target member with a new target member. Initial removal thresholds that alter the characteristics of the system may be particularly advantageous in kits of the present invention where a user may wish to decide the peel strength of the joinder of the mating strong closure deformations, the mating weak closure deformations, or both.

Table 2 shows initial removal values between the components of the four-member system of the present invention. The mating weak closure deformations of, for example, the target member 120 and the adapter 114 join to have an initial removal value designated $\gamma$, where $\gamma_1$ represents an initial removal value between an original target member and an original adapter, $\gamma_2$ represents an initial removal value between the target member and a replacement adapter, and $\gamma_3$ represents an initial removal value between a replacement target member and the replacement adapter. The mating strong closure deformations of, for example, the adapter 114 and the base closure member 108 join to have an initial removal value designated $\beta$, where $\beta_1$ represents an initial removal value between a base closure member and an original adapter, and $\beta_2$ represents an initial removal value between a base closure member and a replacement adapter. A removal value between the base closure member 108 and the supporting backing 102 is referenced as $\alpha_1$, and a removal value between the object member 126 and a buttress 104 may be referenced as $\alpha_2$ when applicable as adapted for near-permanent to permanent affixation. The mating strong closure deformations of, for example, the object member 108 and the target member 114 join to have an initial removal value designated $\delta$, where $\delta_1$ represents an initial removal value between an original target member 114 and an original object member 126, and $\delta_2$ represents an initial removal value between an object member and a replacement target member.

TABLE 2

| (In Pounds per Inch-width) | | | | | | | | |
|---|---|---|---|---|---|---|---|---|
| $\alpha_1$ | $\beta_1$ | $\gamma_1$ | $\alpha_2$ | $\beta_2$ | $\gamma_2$ | $\delta_1$ | $\delta_2$ | $\gamma_3$ |
| 10.0+ | 4.0 | 0.5 | 10.0+ | 4.0 | .25 | 4.0 | 4.0 | 0.1 |
| 6.0+ | 3.5 | 0.25 | 6.0+ | 3.5 | .5 | 3.5 | 3.5 | 0.2 |
| 6.0+ | 3.0 | 0.25 | 6.0+ | 3.0 | .25 | 3.0 | 3.0 | 0.25 |
| 6.0+ | 2.5 | 0.25 | 6.0+ | 2.5 | .1 | 2.5 | 2.5 | 0.25 |
| 6.0+ | 2.0 | 0.2 | 6.0+ | 2.0 | .2 | 2.0 | 2.0 | 0.4 |
| 6.0+ | 2.5 | 0.1 | 6.0+ | 2.5 | .1 | 2.5 | 2.5 | 0.5 |

Although the present invention has been described in considerable detail with reference to certain preferred versions thereof, other versions would be readily apparent to those of ordinary skill in the art. Therefore, the spirit and scope of the appended claims should not be limited to the description of the preferred versions contained herein.

What is claimed is:

1. A method for maintaining a fastening system, said method comprising:
   binding a base closure member on a supportive backing with a base binding system having an initial removal threshold from said supportive backing of $\alpha_1$, said base closure member having a base closure surface comprising base closure engagement members;
   removably affixing a strong adapter closure surface of a substantially planar adapter to said base closure surface, wherein said adapter includes a weak adapter closure surface opposite said strong adapter closure surface and having weak adapter closure engagement members, wherein said strong adapter closure surface comprises strong adapter engagement members adapted to mate with said base closure engagement members to provide an initial removal threshold of $\beta_1$, and wherein $0.01\alpha_1 < \beta_1 < 0.75\alpha_1$;

removably attaching a weak target closure surface of a target member, wherein said weak target closure surface comprises weak target closure engagement members adapted to mate with said weak adapter closure engagement members to provide an initial removal threshold of $\gamma_1$, and wherein $\gamma_1 < 0.5\beta_1$; and replacing said adapter with a replacement adapter upon substantial diminishment of said removal threshold between said weak target closure engagement members and said weak adapter closure engagement members, wherein said replacement adapter includes a weak replacement adapter closure surface opposite a strong replacement adapter closure surface and having weak replacement adapter closure engagement members, wherein said strong replacement adapter closure surface comprises strong replacement adapter engagement members adapted to mate with said base closure engagement members to provide an initial removal threshold of $\beta_2$, wherein $0.01\alpha_1 < \beta_2 < 0.75\alpha_1$, wherein said weak target closure engagement members are adapted to mate with said weak replacement adapter closure engagement members to provide an initial removal threshold of $\gamma_2$, and wherein $\gamma_2 < 0.5\beta_2$.

2. The method of claim 1 further comprising removably coupling a strong target closure surface, opposite said weak target closure surface, of said target member to an object closure surface, comprising object closure engagement members, of an object closure member bound to a buttress by an object binding system having an initial removal threshold from said buttress of $\alpha_2$, and wherein said strong target closure surface comprises strong target engagement members adapted to mate with said object closure engagement members to provide an initial removal threshold of $\delta_1$, and wherein $0.01\alpha_2 < \delta_1 < 0.75\alpha_2$.

3. The method of claim 2 further comprising replacing said target member with a replacement target member upon substantial deterioration of said removal threshold between said weak adapter closure engagement members and said weak target member closure engagement members, wherein said replacement target member includes a weak replacement target member closure surface opposite a strong replacement target member closure surface and having weak replacement target member closure engagement members, wherein said strong replacement target member closure surface comprises strong replacement target engagement members adapted to mate with said object closure engagement members to provide an initial removal threshold of $\delta_2$, wherein $0.01\alpha_2 < \delta_2 < 0.75\alpha_2$, wherein said weak adapter closure engagement members are adapted to mate with said weak replacement target member closure engagement members to provide an initial removal threshold of $\gamma_3$, and wherein $\gamma_3 < 0.5\delta_2$.

4. The method of claim 1 wherein said removably affixing step includes removably affixing strong adapter with said base closure engagement members to provide an initial removal threshold of $\beta_1$, wherein $0.1\alpha_1 < \beta_1 < 0.75\alpha_1$.

5. The method of claim 4 wherein said removably affixing step includes removably affixing strong adapter with said base closure engagement members to provide an initial removal threshold of $\beta_1$, wherein $0.1\alpha_1 < \beta_1 < 0.5\alpha_1$.

6. A method for maintaining a fastening system, said method comprising: binding a base closure member on a supportive backing with a base binding system having an initial removal threshold from said supportive backing of $\alpha_1$, said base closure member having a base closure surface comprising base closure engagement members removably affixing a strong adapter closure surface of a substantially planar adapter to said base closure surface, wherein said adapter includes a weak adapter closure surface opposite said strong adapter closure surface and having weak adapter closure engagement members wherein said strong adapter closure surface comprises strong adapter engagement members adapted to mate with said base closure engagement members to provide an initial removal threshold of $\beta_1$, wherein $\beta_1 < \alpha_1$ to a degree that permits removal of said strong adapter engagement members from said base closure deformations without substantially disjoining said base closure member from said supportive backing; and removably attaching a weak target closure surface of a target member, wherein said weak target closure surface comprises weak target closure engagement members adapted to mate with said weak adapter closure engagement members to provide an initial removal threshold of $\gamma_1$, and wherein $\gamma_1 < \beta_1$ to a degree that permits removal of said weak target closure engagement members from said weak adapter closure engagement members without substantially disjoining said strong adapter deformations and said base closure engagement members;

and further comprising the step of replacing said adapter with a replacement adapter upon substantial deterioration of said removal threshold between said weak target closure engagement members and said weak adapter closure engagement members, wherein said replacement adapter includes a weak replacement adapter closure surface opposite a strong replacement adapter closure surface and having weak replacement adapter closure engagement members, wherein said strong members adapter closure surface comprises strong replacement adapter engagement members adapted to mate with said base closure engagement members to provide an initial removal threshold of $\beta_2$, wherein $\beta_2 \geq \alpha_1$, wherein said weak target closure engagement members are adapted to mate with said weak replacement adapter closure engagement members to provide an initial removal threshold of $\gamma_2$, and wherein $\gamma_2 < \beta_2$ to a degree that permits removal of said weak target closure engagement members from said weak replacement adapter closure engagement members without substantially disjoining said strong adapter engagement members from said base closure engagement members.

7. The method of claim 6 further comprising removably coupling a strong target closure surface, opposite said weak target closure surface, of said target member to an object surface, having an object closure surface comprising object closure engagement members, of an object member bound to a buttress by object binding system having an initial removal threshold from said buttress of $\alpha_2$, and wherein said strong target closure surface comprises strong adapter engagement members adapted to mate with said object closure engagement members to provide an initial removal threshold of $\delta_1$, and wherein $\delta_1 < \alpha_2$ and $\delta_1 \geq \alpha_2$ to a degree that permits removal of said strong target engagement members from said object closure engagement members without substantially disjoining said object binding system.

8. The method of claim 7 further comprising replacing said target member with a replacement target member upon substantial deterioration of said removal threshold between said weak adapter closure engagement members and said weak target member closure engagement members, wherein said replacement target member includes a weak replacement target member closure surface opposite a strong replacement target member closure surface and having weak replacement target member closure engagement members, wherein said strong replacement target member closure surface comprises strong replacement target engagement members adapted to mate with said object closure engagement members to provide an initial removal threshold of $\delta_2$, wherein $\delta_2 \geq \alpha_2$, wherein said weak replacement adapter closure engagement members are adapted to mate with said weak replacement target member closure engagement members to provide an initial removal threshold of $\gamma_3$, and wherein $\gamma_3 < \delta_2$.

9. A fastening for providing variable fastening ability and structural longevity, said kit comprising:
   a supportive backing;
   a base closure member, affixed by a base binding system to said supportive backing with an initial removal threshold of $\alpha_1$, having a base closure surface with base closure engagement members;
   a substantially planar adapter member with a strong adapter closure surface having strong adapter closure engagement members adapted to removably affix to said base closure engagement members with an initial removal threshold of $\beta_1$, and with a weak adapter closure surface opposite said strong adapter closure surface and having weak adapter closure engagement members, and wherein $\beta_1 < \alpha_1$ to a degree that permits removal of said strong adapter engagement members from said base closure engagement members without substantially disjoining said base closure member from said supportive backing;
   a target member with a weak target closure surface having weak target closure engagement members adapted to removably attach to said weak adapter closure engagement members to provide an initial removal threshold of $\gamma_1$, and wherein $\gamma_1 < \beta_1$ to a degree that permits removal of said weak target closure engagement members from said weak adapter closure engagement members without substantially disjoining said strong adapter engagement members and said base closure
   wherein said target member is substantially planar and further includes a strong target closure surface opposite said weak target closure surface and having strong target engagement members and further comprising an object closure member, with an object closure surface having object closure engagement members, bound to a buttress by an object binding system having an initial removal threshold from said buttress of $\alpha_2$, and wherein said strong target engagement members are adapted to mate with said object closure engagement members to provide an initial removal threshold of $\delta_1$, and wherein $\delta_1 < \alpha_2$ to a degree that permits removal of said strong target engagement members from said object closure engagement members without substantially disjoining said object binding system.

10. The kit of claim 9 further comprising a replacement target member with a weak replacement target closure surface having weak replacement target closure engagement members adapted to removably attach to said weak adapter closure engagement members to a degree that permits removal of said weak replacement target closure engagement members from said weak adapter closure without substantially disjoining said strong adapter engagement members and said base closure engagement members.

* * * * *